United States Patent [19]
Downey et al.

[11] Patent Number: 5,891,012
[45] Date of Patent: Apr. 6, 1999

[54] CORONARY ARTERY COUNTERPULSATION DEVICE AND METHOD

[75] Inventors: H. Fred Downey; Xiaoming Bian, both of Fort Worth, Tex.

[73] Assignee: My-Tech, Inc., Newport Beach, Calif.

[21] Appl. No.: 82,559

[22] Filed: May 21, 1998

[51] Int. Cl.⁶ ............................................. A61M 1/10
[52] U.S. Cl. .............................. 600/17; 604/98; 604/99; 604/102; 600/18
[58] Field of Search ................... 600/16–18; 606/192, 606/194; 604/8, 9, 19, 27, 34, 65–67, 93, 96–99, 101, 102; 623/3

[56] References Cited

U.S. PATENT DOCUMENTS

| | | | |
|---|---|---|---|
| 4,154,227 | 5/1979 | Krause et al. | 600/18 |
| 4,459,977 | 7/1984 | Pizon et al. | 600/18 |
| 4,531,936 | 7/1985 | Gordon | 600/18 |
| 4,648,384 | 3/1987 | Schmukler | 600/18 |
| 4,697,574 | 10/1987 | Karcher et al. | 600/18 |
| 4,785,795 | 11/1988 | Singh | 600/18 |
| 4,804,358 | 2/1989 | Karcher et al. | 600/17 |
| 5,163,910 | 11/1992 | Schwartz et al. | 604/151 |
| 5,195,942 | 3/1993 | Weil et al. | 600/18 |
| 5,287,861 | 2/1994 | Wilk | 128/898 |
| 5,312,344 | 5/1994 | Grinfeld et al. | 604/101 |
| 5,383,854 | 1/1995 | Safar et al. | 604/98 |
| 5,395,353 | 3/1995 | Scribner | 604/264 |
| 5,425,708 | 6/1995 | Nasu | 604/96 |
| 5,484,411 | 1/1996 | Inderbitzen et al. | 604/96 |
| 5,484,412 | 1/1996 | Pierpont | 604/101 |

OTHER PUBLICATIONS

Toshihiro Iwamoto et al., "Coronary perfusion related changes in myocardial contractile force and systolic ventricular stiffness," *Cardiovascular Research*, 1994; 28:1331–1336.

H. Fred Downey, "Coronary–Ventricular Interaction: The Gregg Phenomenon", *Cardiac–Vascular Remodeling and Functional Interaction*, Ed. Maryama, Hori, Janicki, Tokyo, 1997, pp. 321–332.

*Primary Examiner*—William E. Kamm
*Assistant Examiner*—Kennedy J. Schaetzle
*Attorney, Agent, or Firm*—Charles D. Gunter, Jr.

[57] ABSTRACT

A device and method are shown for improving coronary blood circulation and cardiac contractile function, synchronizing coronary perfusion pressure with the patient's cardiac cycle, by alternately pressurizing and depressurizing an inflatable balloon located within the interior of the device. The device comprises a catheter having a distal end which is installed at the ostium of the coronary artery of a patient. The device is alternately pressurized during the relaxation phase of a patient's cardiac cycle and then depressurized during the contraction phase of the cardiac cycle to thereby modulate the coronary perfusion pressure and blood flow.

15 Claims, 4 Drawing Sheets

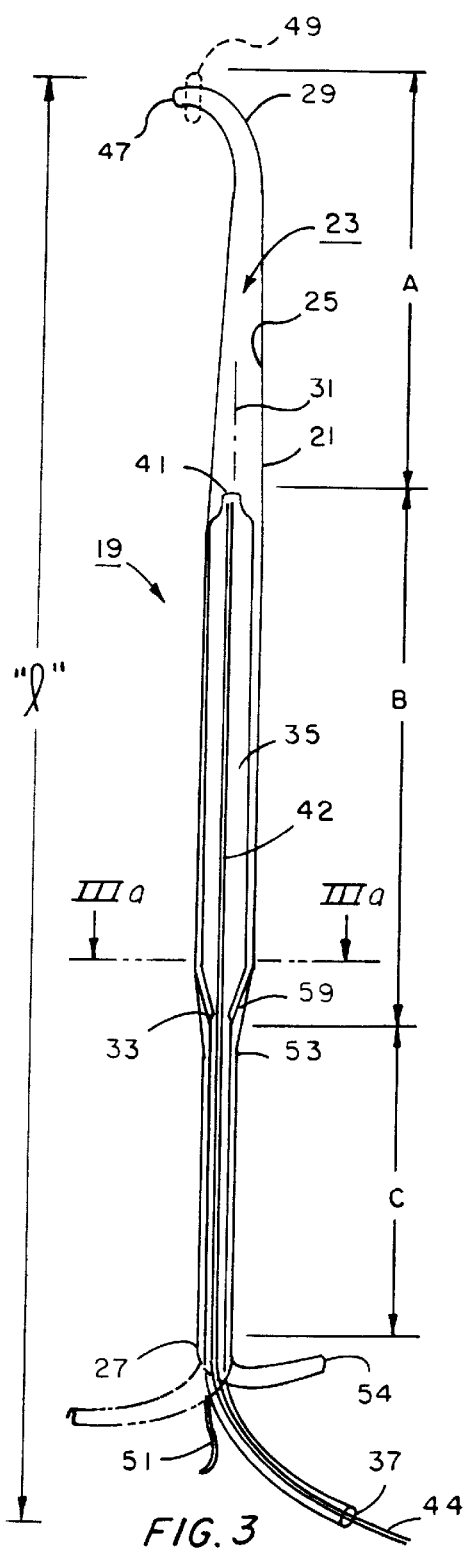
FIG. 3
FIG. 3a
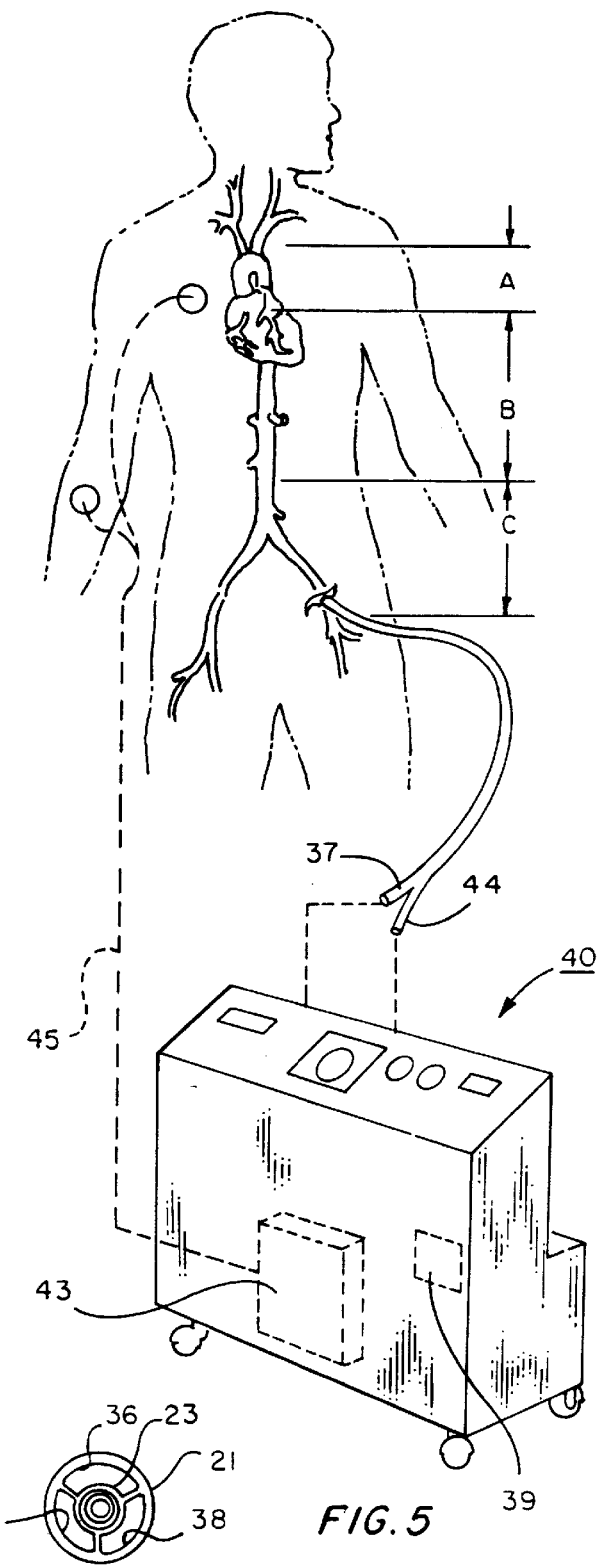
FIG. 5

CORONARY ARTERY COUNTERPULSATION DEVICE AND METHOD

BACKGROUND OF THE INVENTION

1. Field of the Invention

The present invention relates generally to a device and method for varying coronary perfusion pressure to provide therapeutic assistance in cases of insufficiency of coronary circulation and depressed cardiac contractile function.

2. Description of the Prior Art

Approximately ½ million Americans die of acute heart failure annually. Of these deaths, approximately 50% occur in spite of medical treatment (the other 50% do not reach the hospital). Although acute heart failure is presently treated with drugs and other therapy, present interventions are not sufficiently effective. Clearly, additional measures are needed to help save lives of patients suffering from acute heart failure due to obstruction of the coronary vasculature or due to extensive cardiac surgery or other causes.

The coronary circulation system delivers blood to the heart muscle during the relaxation phase of cardiac contraction. During the contraction phase, pressure in the heart muscle rises and restricts coronary inflow, even though the arterial pressure rises due to cardiac ejection of blood. This elevation of coronary pressure increases the stiffness of the heart wall. With increased stiffness, the heart must expend more energy to bend the heart wall in order to eject blood. In other words, contraction of the heart against a large coronary pressure results in more "internal work" relative to the beneficial "external work" of ejecting blood from the heart chamber. This phenomenon has been postulated in the literature with reference to the "Gregg Phenomenon" and also with reference to the "garden hose" effect. The Gregg Phenomenon refers to the observation made in the 1950's by Donald Gregg, a noted American coronary physiologist, that myocardial oxygen consumption varied with coronary perfusion pressure, even when all other determinants of myocardial oxygen demand, such as heart rate and arterial pressure, were held constant. More recent studies have shown that the Gregg Phenomenon results from coronary pressure induced changes in the ventricular systolic stiffness. See, for example, "Coronary Perfusion Related Changes In Myocardial Contractile Force And Systolic Ventricular Stiffness", by Iwamoto, Bai and Downey, *Cardiovascular Research*, 1994; 28:1331–1336. It can be theorized that, when the systolic coronary pressure is decreased, the heart wall becomes less stiff and can be more readily deformed during cardiac contraction. Thus, with reduced coronary pressure during the cardiac phase of contraction, the heart muscle requires less oxygen to overcome this important component of "internal" cardiac work.

The garden hose effect refers to the erectile characteristics of the coronary circulation and parallels the analogy of the Gregg Phenomenon. Alteration of coronary pressure changes the amount of blood in the coronary circulation and affects its rigidity. During cardiac contraction when arterial pressure is highest, the coronary pressure is also high, and this tends to distend the coronary circulation as does turning on a faucet to a garden hose. The garden hose effect is thus directly related to the Gregg Phenomenon. For further background on the Gregg Phenomenon see "Coronary-Ventricular Interaction: The Gregg Phenomenon", by Downey, *Cardiac-Vascular Remodeling and Functional Interaction*, Ed. Maryama, Hori, Janicki, Tokyo, 1997, pp. 321–332.

The present invention has as an object to provide a method and device for varying or modulating coronary perfusion pressure according to the phases of a patient's cardiac cycle. Since perfusion pressure alters myocardial stiffness, changes in systolic stiffness should affect myocardial oxygen demand by changing the ratio of internal to external work. With a decreased systolic perfusion pressure, myocardial oxygen demands will be reduced, thereby permitting an increase in myocardial oxygen utilization efficiency.

Another object of the invention is to provide a coronary counterpulsation device which will limit the energy expensive component of internal work during cardiac contraction, so that under conditions of limited availability of cardiac energy, more of the energy can be devoted to the external work of pumping blood.

Another object of the invention is to provide a device and method which will reduce coronary pressure during the contraction phase and which will also increase coronary pressure and blood flow during the relaxation phase, when coronary flow normally nourishes the heart muscle.

Another object of the invention is to provide a device and method for increasing coronary flow during the relaxation phase of the cardiac cycle which thereby increases flow through primary as well as supplemental, i.e., collateral, blood vessels supplying tissue whose normal source of blood flow has been compromised by coronary artery disease or other causes.

Another object of the invention is to provide a device and method for significantly decreasing cardiac morbidity and mortality.

Another object of the invention is to provide a coronary artery counterpulsation device and method which compliments existing acute heart failure therapies.

SUMMARY OF THE INVENTION

The device of the invention improves cardiac contractile function and coronary blood flow by varying or modulating the coronary artery perfusion pressure. The device of the invention comprises a flexible catheter having a length defining a longitudinal axis, an open interior, a proximate end and a distal end. The catheter has a plurality of window openings provided at spaced circumferential locations at one region along the longitudinal axis thereof for admitting blood into the open interior after the distal end of the catheter has been installed within a coronary vessel. An inflatable balloon is located within the open interior of the catheter. The balloon is inflatable between a deflated state which allows the flow of blood through the open interior thereof and through the window openings and an inflated state in which the balloon covers the window openings to block the flow of blood through the window openings and forces blood from the open interior of the catheter into the coronary artery. An external pump is connected to the device for communicating a pressurized gas to the balloon for inflating and deflating the balloon at predetermined times in the cardiac cycle of the patient being treated. A pressure sensor, carried by the device, detects the cardiac artery perfusion pressure. Synchronizing means are provided for varying the balloon inflation and deflation states in synchrony with a cardiac cycle of the patient being treated.

The distal end of the catheter terminates in a coronary artery perfusion port which is sized for receipt within the coronary ostium of a patient's heart. An inflatable region is located adjacent the port for stabilizing the catheter within the coronary ostium as the coronary artery perfusion pressure is varied during the cardiac cycle of the patient.

A detachable sheath may be provided for temporarily covering the window openings in the catheter during insertion of the device into the arterial circulation of the patient. The sheath is later removed, thereby allowing the flow of blood through the window openings into the open interior of the catheter. An evacuation line is provided as a part of the detachable sheath and communicates with a space formed between the interior of the sheath and the exterior of the device adjacent the window openings thereof. Any trapped air present in the open interior of the device during the insertion of the device within the arterial circulation is bled from the device through the evacuation line prior to removing the detachable sheath.

In the method of the invention, a coronary perfusion device is provided having a coronary perfusion port and associated pressurization means for cyclically varying the coronary perfusion pressure at the perfusion port. The device is installed within the arterial circulation of a patient and is located so that the coronary perfusion port is installed within the ostium of the coronary artery of the patient. A cardiac cycle of the patient is detected and the coronary perfusion pressure is synchronized with the patient's cardiac cycle by alternately pressurizing and depressurizing the device. The synchronizing step serves to pressurize the device during a relaxation phase of the patient's cardiac cycle and alternately depressurize the device during a contraction phase of the patient's cardiac cycle to thereby regulate coronary perfusion pressure.

By increasing coronary pressure during the relaxation phase of the heart cycle, heart tissue is supplied with blood whose normal source of blood flow has been compromised by coronary artery disease or other causes. This increase in coronary pressure during the relaxation phase of the heart cycle is particularly beneficial in cases of limited cardiac contractile function due to inadequate coronary blood flow or to conditions which limit the production of metabolic energy for cardiac work. Such conditions are common in patients suffering from acute heart failure due to obstruction of the coronary vasculature or due to extensive cardiac surgery. The device and method also limit the energy expensive component of internal work during cardiac contraction.

Additional objects, features and advantages will be apparent in the written description which follows.

BRIEF DESCRIPTION OF THE DRAWINGS

FIG. 3 is a side view of the device of the invention showing the parts thereof;

FIG. 3A is a cross-sectional view taken along lines IIIa—IIIa in FIG. 3;

FIG. 5 is a simplified view of the human anatomy showing portions of the arterial circulation and showing the device of the invention connected to an external pump and synchronizer;

DETAILED DESCRIPTION OF THE INVENTION

Figure 1:
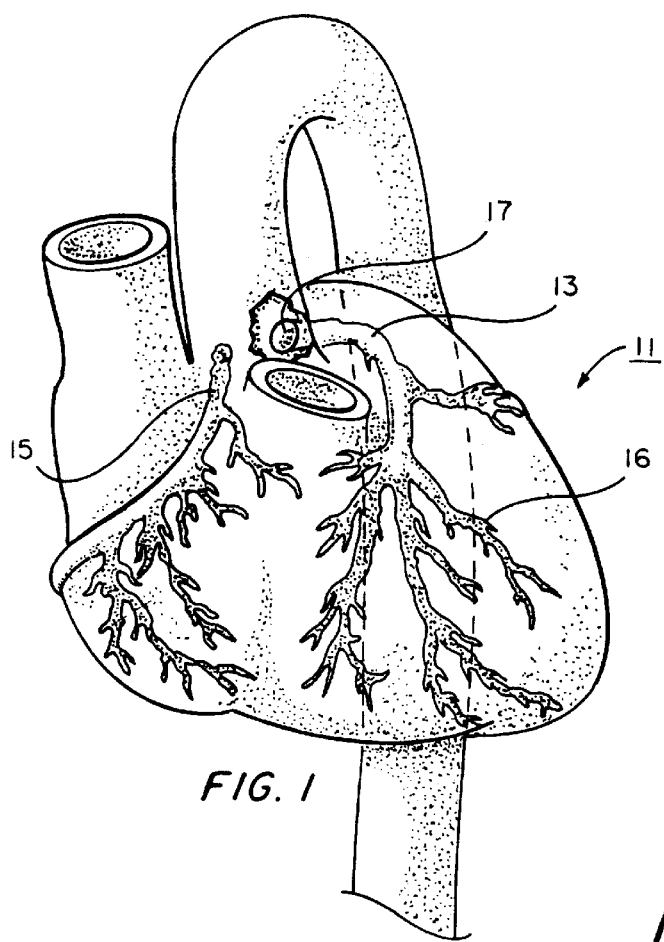
FIG. 1 is a simplified, isolated view of the human heart with its coronary blood supply.

FIG. 1 is a simplified, isolated view of a human heart 11 with its coronary blood supply. The main coronary arteries 13, 15 lie on the surface of the heart while the smaller arteries 16 penetrate from the surface into the cardiac muscle mass. These arteries supply the heart with the majority of its nutritive blood supply since approximately only the inner 75–100 micrometers of the endocardial surface can obtain significant amounts of nutrient directly from the blood in the cardiac chambers.

The left coronary artery 13 supplies mainly the anterior and lateral portions of the left ventricle. The right coronary artery 15 supplies most of the right ventricle as well as the posterior part of the left ventricle in about 80 to 90% of all persons. Most of the venous blood flow from the left ventricle leaves by way of the coronary sinus (not shown) which is about 75% of the total coronary blood flow while most of the venous blood from the right ventricle flows through the small anterior cardiac veins directly into the right atrium, not by way of the coronary sinus. The resting coronary blood flow in the human averages about 225 ml/min, which is about 0.7 to 0.8 ml per gram of heart muscle, or about to 5% of the total cardiac output.

Figure 2:
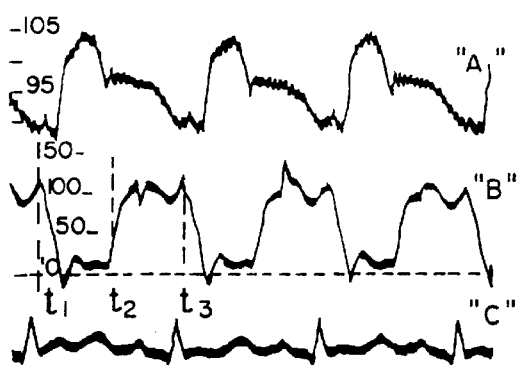
FIG. 2 is a graphical representation of the normal phasic changes in coronary perfusion pressure provided by aortic pressure and coronary blood flow.

FIG. 2 is a graphical representation of the phasic changes in coronary flow which occur during cardiac contraction. See Marston, E. L., C. A. Barefoot, and M. P. Spencer, "Noncannulating Measurements of Coronary Blood Flow", Surg. Forum 10: 636–639, 1959. The upper trace "A" is aortic blood pressure. The middle trace "B" is phasic coronary flow. The lower trace "C" is EKG. The average blood flow is given in milliliters per minute during the phases of the cardiac cycle. The systole portion of the cycle is generally that time period represented between $t_1$ and $t_2$, while the diastole portion of the cycle is represented between the times $t_2$ and $t_3$. Blood flow in the left ventricle falls to a low value during systole, which is opposite to the flow in the other vascular regions of the body. This effect results from the strong compression of the left ventricular muscle around the intramuscular vessels during systole. During the diastole phase of the cardiac cycle, the cardiac muscle relaxes so that blood flow is no longer obstructed through the left ventricular capillaries. Blood flow through the coronary capillaries of the right ventricle also undergo similar phase changes during the cardiac cycle. However, the force of contraction of the right ventricle is far less than that of the left ventricle and the phasic changes illustrated in FIG. 2 are not as apparent.

Figure 4:
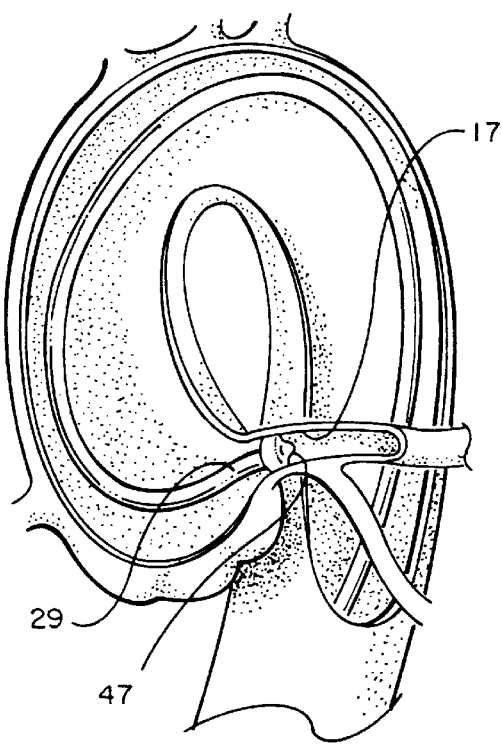
FIG. 4 is a simplified, partially schematic view of a portion of the heart and coronary artery of the heart with the device of the invention installed at the coronary ostium.

FIG. 3 is a side view of the device of the invention designated generally as 19. The device 19 is a catheter, i.e., a flexible tube 21 having a length ("l" in FIG. 3), an open interior 23 defined by the internal sidewalls 25 of the device, a proximate end 27 and a distal end 29. A detachable sheath 53, to be described more fully with respect to FIGS. 4 and 5, is arranged about the proximate end and is shown split apart at 54 in FIG. 3 for ease of illustration of the parts of the device. The catheter or tube 21 can conveniently be formed of a flexible, commercially available plastic having an internal diameter on the order of ¼–⅜ inches. The length of the device defines a longitudinal axis 31.

As shown in FIG. 3 and in exaggerated fashion in FIGS. 6–9, the catheter has at least one window opening 33 at the proximal end thereof. Preferably, the device has a plurality of window openings, in this case three openings (34, 36, 38 in FIG. 3A), provided at equidistantly spaced circumferential locations at one region at the proximate end along the longitudinal axis 31 for admitting blood into the open interior 23 after the distal end of the catheter has been installed within a coronary vessel of a patient.

An inflation means, such as the inflatable balloon 35 is located within the open interior 23 of the catheter 21. The balloon 35 is inflatable between a deflated state shown in FIGS. 6 and 8 which allows the flow of blood through the open interior of the device and through the window openings 33 and an inflated state (FIGS. 7 and 9) in which the balloon covers the window openings 33 to block the flow of blood through the window openings and to force blood into the coronary circulation.

A pressurizing means, such as pump 39 (FIG. 5) provided as a part of a synchronizing unit 40, communicates with the balloon 35 through the inflation line 37. The pump is used to supply a pressurized gas, such as helium, to the interior of the inflatable balloon 35.

A pressure sensor is carried by the device for detecting cardiac artery perfusion pressure. In the embodiment of FIG. 3, an opening 41 in an internal tube 42 communicates by means of outlet line 44 with a standard pressure transducer in conventional fashion. A synchronizer (illustrated schematically at 43 in FIG. 5) varies the balloon inflation and deflation states in synchrony with a cardiac cycle of a patient being treated with the device.

The external pump 39 and synchronizer 43 are commercially available as a combined unit and have been used for many years in patients which cardiogenic shock. Any suitable commercially available device can be utilized for varying the pressure in the balloon 35 in synchrony with the cardiac cycle illustrated in FIG. 2 and as will be explained more fully hereafter.

In addition to the pressure sensor 41 used to monitor the coronary pressure, additional input 45 from an electrocardiogram of the patient will be used to control the synchronizer. Thus, with reference to FIG. 2, the synchronizer 43 would signal the pump 39 authorization to deflate the balloon 35 only between the times illustrated at $t_1$ and $t_2$ in FIG. 2 and would inflate the balloon during the time period between $t_2$ and $t_3$.

As shown in FIG. 3, the distal end 29 of the catheter terminates in a coronary artery perfusion port 47 which is sized for receipt within a coronary ostium (17 in FIGS. 1 and 4) of a patient's heart. An inflatable region, such as inflatable donut 49, is located adjacent the port 47 for stabilizing the catheter 21 within the coronary ostium 17 as coronary artery perfusion pressure is varied during the cardiac cycle of the patient. The donut 49 is inflated by means of an inflation line 51 which runs along the sidewall of the device to the donut 49 for communicating a physiological saline solution to the donut interior. This can be accomplished, e.g., by means of an external syringe (not shown).

FIGS. 6–9 are enlarged views of the device of the invention with portions thereof shown in exaggerated fashion for ease of illustration. The detachable sheath 53 (FIG. 6) is used to temporarily cover the window openings 33 in the catheter 21 during insertion of the device into the aorta of the patient. The sheath 53 can be of a suitable thin plastic and can be, for example, heat shrunk at a distal end 55 thereof to temporarily affix the sheath about the external surface of the catheter adjacent the window openings 33. The sheath 53 is later removed, after the device has been inserted into the arterial circulation, by simply pulling and separating the sheath 53 from the catheter 21 to allow the flow of blood from the arterial circulation or aorta through the window openings 33 into the open interior 25 of the device.

An evacuation line (shown in dotted lines as 60 in FIG. 7) will communicate with an interior space 59 formed between the interior sidewalls 61 of the sheath 53 and the external sidewalls 63 of the device. In this way, any air trapped in the open interior 23 of the device during insertion of the device within the arterial circulation can be bled from the device through the interior space 59 and evacuation line, as by drawing off with a syringe attached to the evacuation line.

Figure 6:
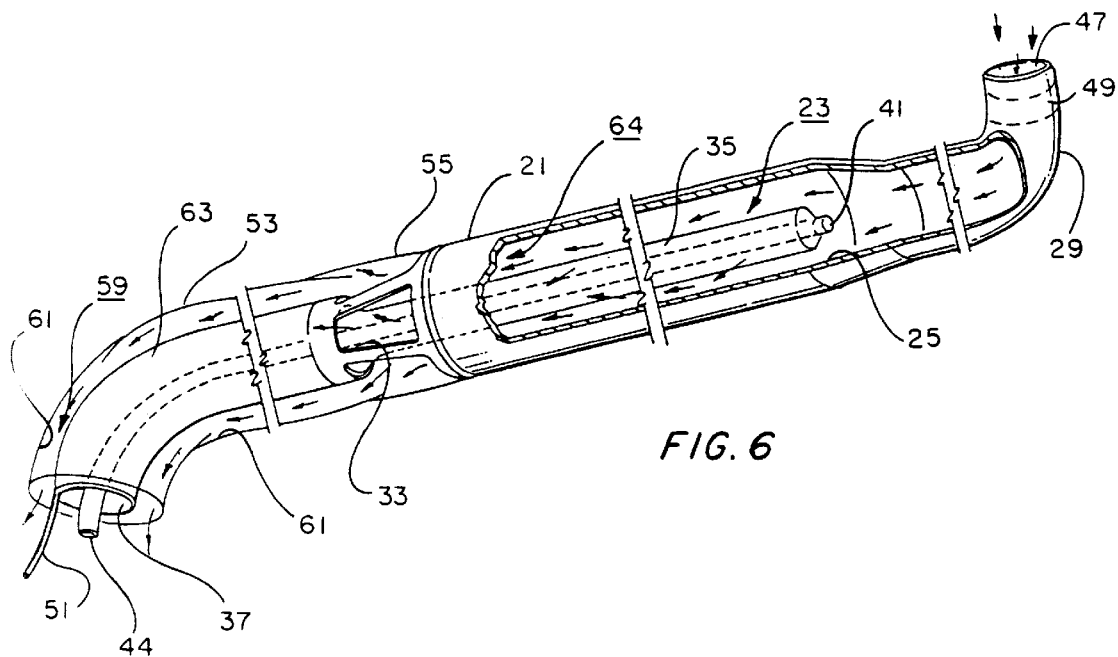
FIG. 6 is a side, exaggerated view of the device of the invention, partly broken away, showing the first step in the placement of the device within a coronary vessel.

FIG. 6 illustrates the device of the invention during insertion, for example through the femoral artery in the groin region on its way to its ultimate location at the coronary ostium. Note that the removable sheath 53 is in place and that any air within the perfusion port 47 or within the interior of the device can be drawn off through the evacuation line 60. The arrows represent the blood flow through the device during the installation step. Note that the balloon 35 is in the relaxed or deflated state and that the donut 49 is also relaxed.

Figure 7:
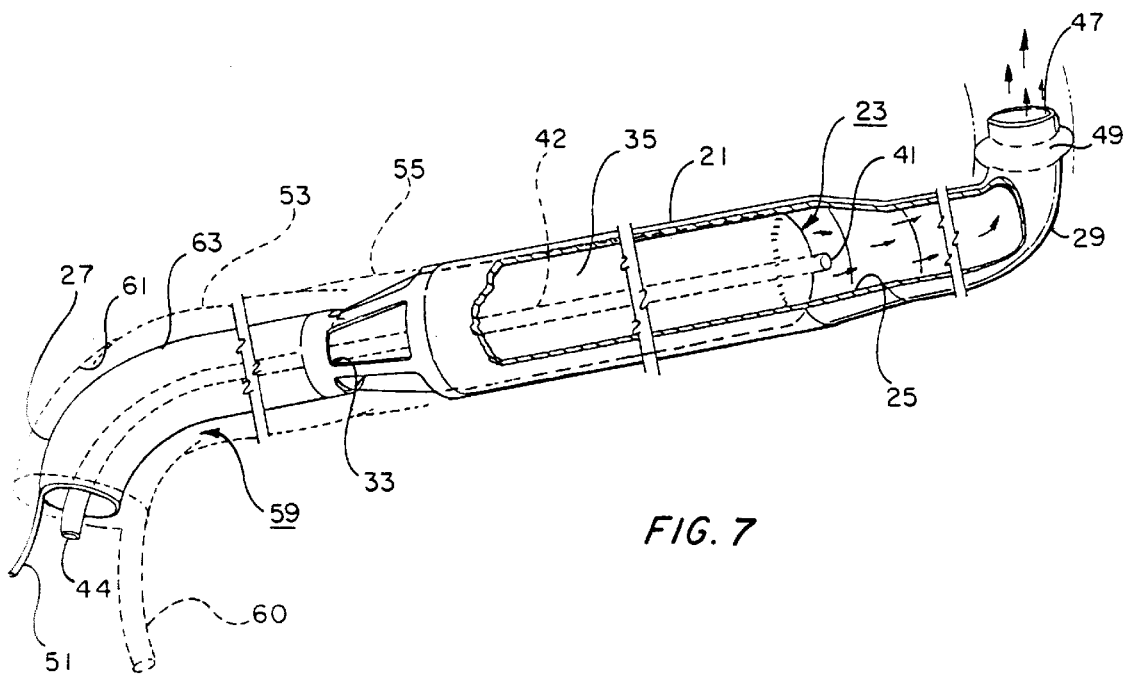
FIG. 7 is a view similar to FIG. 6 showing the second step in the placement of the device in which the detachable sheath is removed.

FIG. 7 schematically illustrates the removal of the detachable sheath 53, thereby exposing the windows 33. The sheath 53 will be removed before the catheter is advanced completely into the aorta and before positioning in the coronary ostium. The relative position of the device with respect to the human arterial circulation is illustrated in FIGS. 3 and 5 with the portions of the length of the device shown as A, B and C.

Once the sheath (shown in imaginary lines) is removed, FIG. 7 shows the device as it would be in place with the perfusion port 47 located at the inlet to the coronary ostium 17 and with the donut 49 inflated by the application of saline through the inflation line 51. Inflation of the donut 49 retains the catheter in place when coronary artery perfusion pressure is varied during the cardiac cycle. The donut 49 is deflated to remove the catheter at the completion of the procedure.

Figure 8:
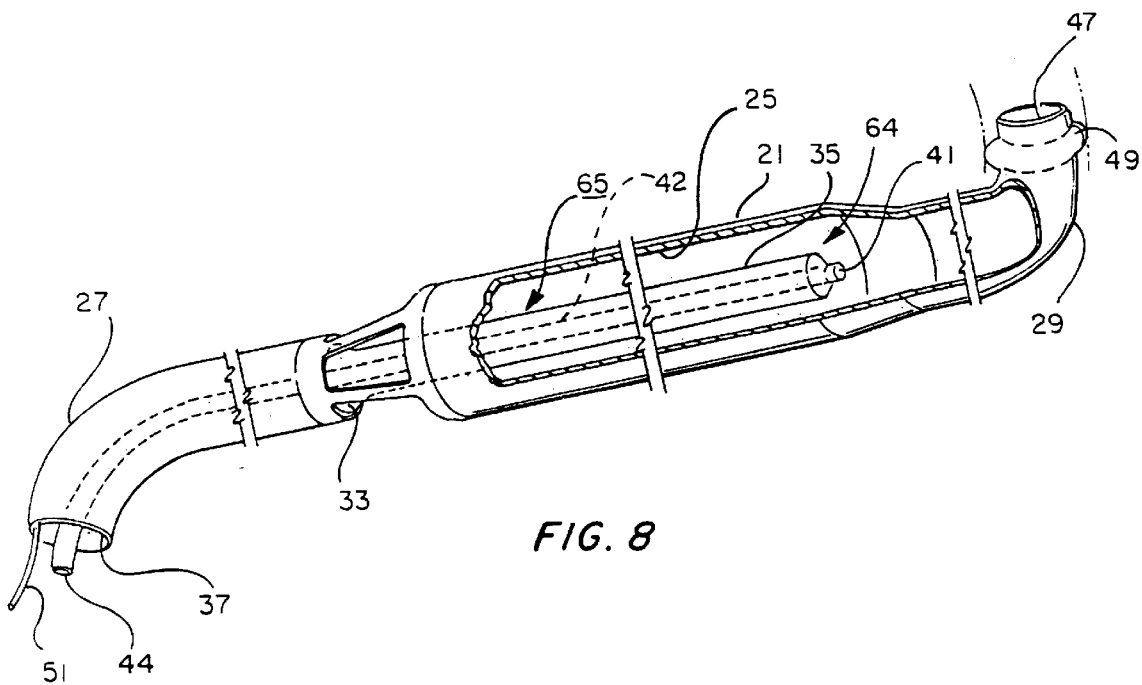
FIG. 8 is a view similar to FIG. 7 showing the operation of the device during the systolic phase of the cardiac cycle.
Figure 9:
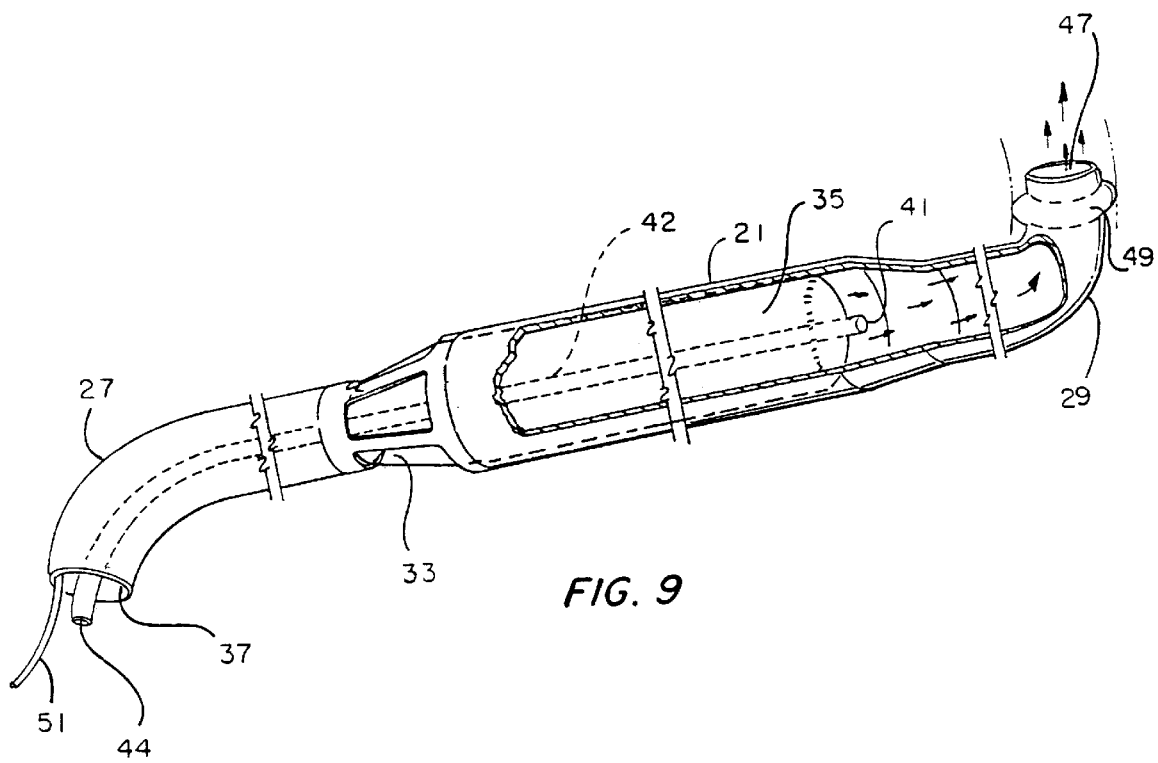
FIG. 9 is a view similar to FIG. 8 showing the operation of the device during the diastolic phase of the cardiac cycle.

The operation of the device will now be briefly described with respect to FIGS. 8 and 9. FIG. 8 shows the device during systole (ventricular contraction) while FIG. 9 shows the device during diastole (ventricular relaxation). Pressure in the balloon 35 is varied during the cardiac cycle through the inflation line 37 which communicates with the pump 39 and synchronizer 43, the pump being synchronized to the heartbeat of the patient. The balloon will be deflated during systole, FIG. 8. Deflation of the balloon will transiently reduce pressure in the internal space (65 in FIG. 8) between the exterior of the balloon and the internal sidewalls 25 of the catheter 21. This action serves to draw blood into the space 65 from (1) the window openings 33; and (2) the coronary circulation through the perfusion port 47, as illustrated by the arrows in FIG. 8.

During the diastole phase illustrated in FIG. 9, inflation of the balloon 35 closes the window openings 33 so blood is forced into the coronary circulation through the perfusion port 47.

The evacuation line (60 in FIG. 7) allows air to be removed the interior space 64 of the device and the space 59 as the catheter 21 is first introduced into the patient's arterial circulation. Blood will enter the space 64 through the perfusion port 47 (which has not yet been positioned into the coronary artery ostium), thereby displacing air which passes outward through the windows 33 (which have not yet entered the arterial circulation). When all of the air has been removed, the balloon 35 will be inflated (as shown in FIG. 7) to cover the windows 33 (blood entry ports). The air removal or evacuation line 60 and sheath 53 will then be detached from the outer wall of the catheter and the catheter will be inserted completely into the patient's arterial circulation. The balloon 35 remains inflated during this phase of the insertion procedure.

The distal end 29 of the catheter 21 is installed within the ostium 17 of the patient's coronary artery with fluoroscopic observation and conventional techniques for coronary artery catheterization. A cardiac cycle of the patient is detected and the coronary perfusion pressure is synchronized with the patient's cardiac cycle by alternately pressurizing and depressurizing the balloon 35 within the device 21. The synchronizing step serves to pressure the device during a relaxation phase of the patient's cardiac cycle (the time between $t_2$ and $t_3$ in FIG. 2) and alternately depressurize the device during a contraction phase of the patient's cardiac cycle (the time between $t_1$ and $t_2$ in FIG. 2) to thereby regulate or modulate cardiac perfusion pressure.

An invention has been provided with several advantages. The device of the invention is simple in design and economical to manufacture and works in harmony to compliment existing therapeutic procedures. The device serves to limit the energy expensive component of internal work during cardiac contraction, so that under conditions of limited availability of cardiac energy, more of the energy can be devoted to the external work of pumping blood. These objects are accomplished by providing a device which reduces coronary pressure during the contraction phase of the cardiac cycle and also increase coronary pressure during the relaxation phase, when the coronary flow normally nourishes the heart muscle. The increase in coronary flow during the relaxation phase of the cardiac cycle should also serve to increase flow through primary as well as supplemental, i.e., collateral blood vessels supplying tissue whose normal source of blood flow has been compromised by coronary artery disease or other causes. The increase in coronary pressure during the relaxation phase of the heart cycle is particularly beneficial in cases of limited cardiac contractile function due to inadequate coronary blood flow or to conditions which limit the production of metabolic energy for cardiac work. The use of the proposed coronary counterpulsation device should decrease cardiac morbidity and mortality, thereby saving lives.

While the invention has been shown in only one of its forms, it is not thus limited but is susceptible to various changes and modifications without departing from the spirit thereof.

What is claimed is:

1. A device for improving coronary blood circulation and cardiac contractile function comprising:

a flexible tube having a length, an open interior, a proximate end and a distal end, the tube having at least one window opening along the length of the said flexible tube for admitting blood into the open interior after the tube has been installed within the arterial circulation;

an inflatable balloon located within the open interior of the tube, the balloon being inflatable through an inflation line between a deflated state which allows the flow of blood through the open interior thereof and through the at least one window opening and an inflated state in which the balloon covers the at least one window opening to block the flow of blood through the at least one window opening and to force blood into the coronary circulation;

an external pump connected to the inflation line for alternately inflating and deflating the balloon;

pressure sensing means connected to the flexible tube for detecting coronary pressure;

synchronizing means for varying the balloon inflation and deflation in synchrony with the cardiac cycle of a patient being treated with the device.

2. The device of claim 1, wherein the flexible tube has a longitudinal axis and wherein a plurality of window openings are provided at spaced circumferential locations at one region along the longitudinal axis.

3. The device of claim 2, wherein the distal end of the flexible tube terminates in a coronary artery perfusion port which is sized for receipt within a coronary ostium of a patient's heart, and wherein an inflatable donut is located adjacent the port for stabilizing the tube within the coronary ostium as coronary artery perfusion pressure is varied during the cardiac cycle of the patient.

4. The device of claim 3, further comprising:

a detachable sheath for temporarily covering the window openings in the tube during insertion of the device within the coronary artery of a patient, the sheath being later removable for allowing the flow of blood through the at least one window opening into the open interior of the flexible tube.

5. The device of claim 4, further comprising:

an evacuation line provided as a part of the detachable sheath and communicating with a space formed between the interior of the sheath and the exterior of the device adjacent the at least one window opening thereof, whereby any air trapped in the open interior of the flexible tube during the insertion of the device within the arterial circulation can be bled from the flexible tube through the evacuation line.

6. A device for varying coronary artery perfusion pressure, comprising:

a flexible catheter having a length defining a longitudinal axis, an open interior, a proximate end and a distal end, the catheter having a plurality of window openings provided at spaced circumferential locations at one region along the longitudinal axis thereof for admitting blood into the open interior after a portion of the catheter has been installed within a coronary vessel;

an inflatable balloon located within the open interior of the catheter, the balloon being inflatable between a deflated state which allows the flow of blood through the open interior thereof and through the window openings and an inflated state in which the balloon covers the window openings to block the flow of blood through the window and force blood to flow into the coronary circulation;

an external pump connected to the inflatable balloon for communicating a pressurized gas to the balloon for inflating and deflating the balloon;

a pressure sensor connected to the catheter for detecting cardiac artery perfusion pressure;

a synchronizer for varying the balloon inflation and deflation states in synchrony with a cardiac cycle of a patient being treated with the device.

7. The device of claim 6, wherein the distal end of the catheter terminates in a coronary artery perfusion port which is sized for receipt within a coronary ostium of a patient's heart, and wherein an inflatable donut is located adjacent the port for stabilizing the catheter within the coronary ostium as coronary artery perfusion pressure is varied during the cardiac cycle of the patient.

8. The device of claim 7, further comprising:

a detachable sheath for temporarily covering the window openings in the catheter during insertion of the device within the arterial circulation of a patient, the sheath being later removable for allowing the flow of blood through the window openings into the open interior of the catheter.

9. The device of claim 8, further comprising:

an evacuation line provided as a part of the detachable sheath and communicating with a space formed between the interior of the sheath and the exterior of the catheter adjacent the window openings thereof, whereby any air trapped in the open interior of the catheter during the insertion of the device within the arterial circulation can be bled from the device through the evacuation line.

10. A method of improving coronary blood circulation and cardiac contractile function the method comprising the steps of:

providing a coronary perfusion device having a coronary perfusion port and associated pressurization means for cyclically varying the coronary perfusion pressure at the perfusion port;

installing the device within the arterial circulation of a patient and locating the coronary perfusion port within the ostium of the coronary artery of the patient;

detecting a cardiac cycle of the patient;

synchronizing the coronary perfusion pressure with the patient's cardiac cycle by alternately pressurizing and depressurizing the device.

11. The method of claim 10, wherein the synchronizing step serves to pressurize the device during a relaxation phase of the patient's cardiac cycle and alternately depressurize the device during a contraction phase of the patient's cardiac cycle to thereby regulate cardiac perfusion pressure.

12. A method of improving coronary blood circulation, the method comprising the steps of:

installing a distal end of a catheter into the ostium of a coronary artery of a patient, the catheter having an inflatable balloon located within an interior space thereof and having an opposite, proximate end provided with at least one window opening for admitting arterial blood to the interior space thereof;

detecting a cardiac cycle of the patient;

synchronizing coronary perfusion pressure with the patient's cardiac cycle by alternately pressurizing and depressurizing the balloon within the device, the synchronizing step serving to pressurize the device during a relaxation phase of the patient's cardiac cycle and alternately depressurize the device during a contraction phase of the patient's cardiac cycle to thereby regulate cardiac perfusion pressure.

13. A method for varying coronary artery perfusion pressure, the method comprising the steps of:

providing a flexible catheter having a length defining a longitudinal axis, an open interior, a proximate end and a distal end, the catheter being provided with a plurality of window openings at spaced circumferential locations at one region along the longitudinal axis thereof for admitting blood into the open interior after the catheter has been installed within a coronary artery of a patient, and wherein the distal end of the catheter terminates in a coronary artery perfusion port which is sized to be installed within a coronary ostium of a patient's heart;

providing an inflatable balloon within the open interior of the catheter, the balloon being inflatable between a deflated state which allows the flow of blood through the open interior thereof and through the window opening and an inflated state in which the balloon covers the window openings to block the flow of blood through the window opening and forcing blood to flow into the coronary circulation;

connecting an external pump to the device for communicating a pressurized gas to the balloon for inflating and deflating the balloon;

locating a pressure sensor on the device for detecting coronary arterial perfusion pressure;

providing a synchronizer for varying the balloon inflation and deflation states in synchrony with a cardiac cycle of the patient;

installing the perfusion port of the catheter within the coronary ostium of the patient's heart, the catheter being provided with an inflatable region located adjacent the port for stabilizing the catheter within the coronary ostium as coronary artery perfusion pressure is varied during the cardiac cycle of the patient;

synchronizing coronary perfusion pressure with the patient's cardiac cycle by alternately pressurizing and depressurizing the balloon within the device, the synchronizing step serving to pressurize the device during a relaxation phase of the patient's cardiac cycle and alternately depressurize the device during a contraction phase of the patient's cardiac cycle to thereby regulate coronary perfusion pressure.

14. The method of claim 13, further comprising the step of:

surrounding the window openings in the catheter with a removable sheath during insertion of the device within the coronary artery of a patient, the sheath being later removed for allowing the flow of blood through the window openings into the open interior of the catheter.

15. The method of claim 14, further comprising the steps of:

attaching an evacuation line to the detachable sheath in communication with a space formed between the interior of the sheath and the exterior of the device adjacent the window openings thereof, whereby any air trapped in the open interior of the device during the insertion of the device within the coronary artery can be bled from the device through the evacuation line.

* * * * *